United States Patent
Bombardelli

(10) Patent No.: US 9,687,468 B2
(45) Date of Patent: *Jun. 27, 2017

(54) CYNARA SCOLYMUS EXTRACTS FOR THE TREATMENT OF DYSLIPIDAEMIA

(75) Inventor: Ezio Bombardelli, Groppello Cairoli (IT)

(73) Assignee: INDENA S.P.A., Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 14/342,593

(22) PCT Filed: Sep. 13, 2012

(86) PCT No.: PCT/EP2012/067889
§ 371 (c)(1),
(2), (4) Date: Mar. 31, 2014

(87) PCT Pub. No.: WO2013/037857
PCT Pub. Date: Mar. 21, 2013

(65) Prior Publication Data
US 2014/0228428 A1    Aug. 14, 2014

(30) Foreign Application Priority Data
Sep. 16, 2011    (IT) .............................. MI2011A1670

(51) Int. Cl.
| *A01N 43/16* | (2006.01) |
|---|---|
| *A61K 31/35* | (2006.01) |
| *A61K 31/352* | (2006.01) |
| *A61K 36/28* | (2006.01) |
| *A61K 31/216* | (2006.01) |
| *A61K 31/365* | (2006.01) |

(52) U.S. Cl.
CPC .......... *A61K 31/352* (2013.01); *A61K 31/216* (2013.01); *A61K 31/365* (2013.01); *A61K 36/28* (2013.01)

(58) Field of Classification Search
CPC .. A61K 31/216; A61K 31/352; A61K 31/365; A61K 36/28
See application file for complete search history.

(56) References Cited

U.S. PATENT DOCUMENTS

| 6,162,438 A | 12/2000 | Tomer |
|---|---|---|
| 2008/0220096 A1 | 9/2008 | Bombardelli |

FOREIGN PATENT DOCUMENTS

| EP | 0958828 | 11/1999 |
|---|---|---|
| EP | 1967199 | 9/2008 |
| WO | 03013562 | 2/2003 |
| WO | 2007006391 | 1/2007 |
| WO | WO 2007006391 A2 * | 1/2007 |
| WO | 20090100970 | 8/2009 |

OTHER PUBLICATIONS

Tropical Plant Database, Raintree, Copyrighted 1996, updated Mar. 30, 2010.*
Mercola, The Science is practically screaming . . . Don't Make This Trendy Fat Mistake, Nov. 11, 2011.*
Fritsche et al, Eur. Food Res. Technol. (2002) 215:149-157.*
Clayton South, What Is It? and Where Does It Come From?, Apr. 19, 2007.*
Foster et al, Western Medicinal Plants and Herbs, book, copyrighted 2002.*
Bundy R, et al., Artichoke Leaf Extract (Cynara Scolymus) . . . , Phytomedicine, vol. 15, No. 9, pp. 668-675, 2008.
Noemi Fantini, et al., Evidence of Glycemia-Lowering Effect . . . , Phytotherapy Research 2010.
International Search Report issued in counterpart PCT Application No. PCT/EP2012/067889.
Written Opinion of International Searching Authority issued in counterpart PCT Application No. PCT/EP2012/067889.
Response to the Written Opinion issued by the International Preliminary Examining Authority dated Feb. 3, 2014.
International Preliminary Report on Patentability issued in counterpart PCT Application No. PCT/EP2012/067889.

* cited by examiner

*Primary Examiner* — Jean Cornet
(74) *Attorney, Agent, or Firm* — Silvia Salvadori, P.C.; Silvia Salvadori

(57) ABSTRACT

The present invention relates to the preparation of *Cynara scolymus* leaf extracts, which are useful for the prevention and treatment of dyslipidaemia, in particular to increase HDL cholesterol in patients at cardiovascular risk. Said extracts are useful to normalize the lipid and carbohydrate balances and significantly increase the value of HDL cholesterol by favorably changing the LDL/HDL ratio, especially in post-infarction patients with drug-induced dyslipidaemia.

8 Claims, No Drawings

CYNARA SCOLYMUS EXTRACTS FOR THE TREATMENT OF DYSLIPIDAEMIA

This application is a U.S. national stage of PCT/EP2012/067889 filed on Sep. 13, 2012, which claims priority to and the benefit of Italian Application No. MI2011A001670 filed on Sep. 16, 2011, the contents of which are incorporated herein by reference in their entirety.

SUMMARY OF THE INVENTION

The present invention relates to the preparation of a novel extract of Cynara scolymus with a high content of flavonoids and sesquiterpenes, produced from the leaves of selected cultivars. The extracts of the invention increase the HDL cholesterol and are useful in the treatment of dyslipidaemia in patients at cardiovascular risk. As well as normalising the lipid and carbohydrate balance, the extracts of the invention are also useful to regulate dyspepsia and non-alcoholic liver steatosis. In particular, the extracts have provided to increase the HDL cholesterol value significantly in patients with below-average parametric values, by favourably changing the LDL/HDL ratio.

PRIOR ART

Globe artichoke (Cynara scolymus) extracts are known for their choleretic, cholagogic, anti-dyspepsia and mildly cholesterol-reducing action; the cholesterol reduction is modest (not more than approx. 10%). The published studies differ in terms of quality of protocols and composition of the extracts used.

Obtaining Cynara scolymus extracts presents major problems of reproducibility, because the active ingredient content is not uniform from preparation to preparation. Evaluating the therapeutic activity of the extracts is therefore problematic, and comparisons with other known drugs are difficult, if not impossible. The low reproducibility of the extracts is due to a number of factors, such as the choice of the plant biomass and the conditions used in drying and in the extraction process. The production of the biomass is critical because the drying conditions, which are essential to maintain the active ingredient content, depend on the growing period of the plant.

The active components of artichoke extracts are caffeoylquinic acids, which perform a choleretic, blood-sugar reducing and liver-protecting effect; flavonoids, which perform a hypolipaemic action associated with cholesterol synthesis, and cynaropicrin, which performs an anti-inflammatory action due to interaction with nuclear factor NFkB and TNF-α.

DESCRIPTION OF THE INVENTION

It has now been found that an extract with an active ingredient content that guarantees marked, constant therapeutic activity can be obtained from the leaves of selected artichoke cultivars. It has also been found that the cynaropicrin present in the extract of the invention also acts at hepatic level on the enzymes that regulate HDL biosynthesis.

Young leaves of the selected artichoke cultivar, preferably Cynara scolymus or Cynara carduncolus, preferably Cynara scolymus, are used to prepare the extract of the invention. It is preferable to use the leaves about a month after the germination of the seeds or after transplanting the seedlings. The Cynara species are preferably produced using organic agriculture techniques, avoiding the use of pesticides and monitoring their absence in the growing medium, as pesticide removal would be impossible without simultaneously prejudicing the content of active lipophilic ingredients responsible for modulating the formation of HDL lipoproteins.

A particularly preferred variety of artichoke is the spiny purple variety of Cynara scolymus. A plant biomass, easily dried at temperatures of between 60 and 100° C., preferably 80° C., is obtained from the plant, grown to a foliage height of 20 cm.

The selected cultivar must preferably have a 3.8% content of caffeoylquinic acids, 1.5% luteolin flavonoids and 3% cynaropicrin. After drying, the biomass is extracted by known methods, described, for example, in WO 2007/006391 and WO 2008/107183.

The extracts obtained have a caffeoylquinic acid content of between 30 and 45%, preferably 35±2%, a flavonoid content of 8 to 16%, preferably 12±2%, and a cynaropicrin content of 10 to 18%, preferably 13±2%.

Said extracts have demonstrated an unexpected activity in reducing total cholesterol, LDL cholesterol and blood glucose, and increasing cHDL. More specifically, the extract significantly reduces the fasting blood glucose, total cholesterol and LDL cholesterol levels by 20%, increases diuresis, thus helping to reduce the blood pressure, and contributes to reducing liver steatosis.

In particular, it should be emphasised that an unexpectedly high increase in HDL cholesterol is observed in both hyperlipaemic individuals and those with below-normal HDL cholesterol resulting from statin treatment or cholesterol-lowering drugs. Modest, erratic increases in HDL cholesterol following the administration of Cynara scolymus extracts have been reported in the literature, but without any evidence of reproducibility or consistency. In fact, these studies (Naturmed, 13, 17-24, 1998, Arzneim-Forschung, 50, 260-65, 2000, The Cochrane Library, 2002, Issue 3) report contradictory data of low practical relevance.

Conversely, experimentation with the compositions of the invention indicates a reduction of approx. 20% in total cholesterol and LDL cholesterol, and a significant increase of 19% in HDL cholesterol. This increase, which was found to be constant over time on a case study of patients with total cholesterol ranging from 200 to 280 mg/dl, is not observed with known herbal preparations.

The extract of the invention has also proved effective on various parameters in patients suffering from metabolic syndrome, where normalisation of parameters such as blood glucose, lipid parameters and hypertension was observed.

The extracts of the invention will be formulated in suitable administration forms such as capsules or normal or gastroprotected tablets.

The preferred carriers are oils rich in ω-3 fatty acids which facilitate absorption of the cynaropicrin present in the extract.

According to a further aspect, the compositions of the invention may be administered in combination with other substances having a useful or complementary activity.

The compositions of the invention will be formulated according to conventional methods, such as those described in "Remington's Pharmaceutical Handbook", Mack Publishing Co., N.Y., USA. In particular, the compositions of the invention will be formulated according to conventional plant ingredient formulation techniques, which require particular care to be taken to avoid interactions with the excipients and the capsule matrices. Examples of oral formulations are tablets, dragées, soft and hard gelatin capsules, and cellulose capsules. The average dose corresponds to 100-500 mg of extract one to three times a day.

The following examples illustrate the invention in greater detail.

Example 1—Cellulose Capsules Suitable to Contain Oils

Unit Composition:

| | |
|---|---|
| *Cynara scolymus* extract | 200 mg |
| Glyceryl monostearate | 10 mg |
| Linseed oil | q.s. for 800 mg |
| Soya lecithin | 10 mg |

Example 2—Soft Gelatin Capsules

Unit Composition:

| | |
|---|---|
| *Cynara scolymus* extract | 300 mg |
| Glyceryl monostearate | 10 mg |
| Linseed oil | q.s. for 700 mg |
| Soya lecithin | 10 mg |

Example 3—Tablets

Unit Composition:

| | |
|---|---|
| *Cynara scolymus* extract | 200 mg |
| Microcrystalline cellulose | 300 mg |
| Lactose | 190 mg |
| Silicon dioxide | 5 mg |
| Magnesium stearate | 5 mg |

The invention claimed is:

1. An oral pharmaceutical composition formulated as a tablet, a dragée or a soft hard gelatin capsule comprising extract of the leaves of *Cynara* species varieties having a caffeoylquinic acid content of 30 to 45%, a flavonoid content of 8 to 16% and a cynaropicrin content of 10 to 18%; and
   at least one pharmaceutically acceptable excipient or carrier.

2. The oral pharmaceutical composition according to claim 1, wherein the caffeoylquinic acid content is 35±2, the flavonoid content is 12±2% and the cynaropicrin content is 13±2%.

3. The oral pharmaceutical composition according to claim 1, obtainable from young leaves of selected *Cynara scolymus* or *Cynara carduncolus* cultivars.

4. The oral pharmaceutical composition according to claim 3, obtainable from *Cynara scolymus* cultivars.

5. The oral pharmaceutical composition according to claim 4, wherein the cultivar is the spiny purple variety.

6. A method of treating hyperglycaemia, hypercholesterolemia, hypertension or hepatic steatosis in a patient in need thereof, said method comprising:
   administering an effective amount of the pharmaceutical composition according to claim 1 to said patient; and
   treating said patient.

7. A method of treating hypercholesterolemia in a patient in need thereof, said method comprising:
   administering an effective amount of the pharmaceutical composition according to claim 1 to said patient; and
   changing the LDL/HDL ratio increasing HDL cholesterol said patient.

8. The oral pharmaceutical composition according to claim 1, wherein the carrier is an oil comprising omega-3 unsaturated fatty acids.

* * * * *